(12) United States Patent
Numada

(10) Patent No.: US 6,349,227 B1
(45) Date of Patent: Feb. 19, 2002

(54) NON-INVASIVE LIVING BODY MEASURING APPARATUS AND METHOD

(75) Inventor: Shigehiro Numada, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/422,798

(22) Filed: Oct. 22, 1999

(30) Foreign Application Priority Data

Oct. 23, 1998 (JP) .......................................... 10-340931
Jun. 15, 1999 (JP) .......................................... 11-206626

(51) Int. Cl.$^7$ ................................................ A61B 5/00
(52) U.S. Cl. ...................................... 600/310; 600/309
(58) Field of Search ............................... 600/309–310, 600/322–324, 326, 473, 328, 476

(56) References Cited

U.S. PATENT DOCUMENTS 5,974,338 A * 11/1999 Asano et al. ................ 600/322
6,061,583 A * 5/2000 Ishihara et al. ............. 600/322
6,128,525 A * 11/2000 Zeng et al. .................. 600/476

* cited by examiner

Primary Examiner—Eric F. Winkaur
Assistant Examiner—Matthew Kremer

(57) ABSTRACT

A non-invasive living body measuring apparatus includes an image capturing section for capturing an image of the irradiated portion of the living body. When the image capturing section captures first and subsequent images of a portion of a living body at different times and the data processing section extracts characteristic patterns from the images, and sets an analysis region in the first image, the data processing section sets an analysis region in subsequent images based on a relative shift amount between the characteristic patterns of the first and subsequent image requisite for matching the characteristic patterns to each other.

12 Claims, 14 Drawing Sheets

NON-INVASIVE LIVING BODY MEASURING APPARATUS AND METHOD

Cross-References to Related Applications

This application is related to Japanese patent applications No. HEI 10-340931 filed on Oct. 23, 1998 and No. HEI 11-206626 filed on Jun. 15, 1999 whose priorities are claimed under 35 USC §119, the disclosures of which are incorporated herein by reference in their entireties.

BACKGROUND OF THE INVENTION

1. Field of the Invention

The present invention relates to a non-invasive living body measuring apparatus and method, and more particularly to a non-invasive living body measuring apparatus and method for analyzing image information obtained from a living body irradiated with light to obtain living body information such as morphology of a living body or concentration of a living body component.

2. Description of the Related Art

International Publication No. WO97/24066 discloses an apparatus for measuring a living body component such as hemoglobin without collecting blood (i.e., in a non-invasive manner). In the apparatus, a finger is positioned at a detecting section to capture a transmitted image of the finger, an analysis region (a blood vessel site with good contrast) is set in the image, and the analysis region is analyzed to calculate hemoglobin concentration.

When the finger is removed from the detecting section and placed again at the detecting section, the position of the finger may be different from its previous position. This allows the obtained captured image to be shifted in a right-and-left direction or in an up-and-down direction, rendering it difficult to measure the same site of the living body repeatedly. Therefore, this apparatus maybe unsuitable for measuring the change with time (time-sequential change) in the blood vessel width or the concentration of the living body component on a specific blood vessel site.

For example, Japanese Unexamined Patent Publication No. HEI 07(1995)-21373 discloses an apparatus for personal identification by picking up characteristic points (end points and branching points) from a blood vessel pattern obtained from a captured blood vessel image and using the positional arrangement of the characteristic points, the directional vector of the blood vessel, the linked state among the characteristic points and their combination as characteristic quantities. However, this publication does not disclose any solution to the problem of the shift of the living body in a non-invasive living body measuring apparatus. The publication merely discloses that "It might be expected that the direction of the finger may be shifted between the time of registration and the time of verification, so that a predetermined allowance (tolerance) range may be provided at the time of comparison for the personal identification".

On the other hand, an image processing technique is known in which an image is binarized (digitized) in trying to extract a characteristic feature from the image having a density blur. However, no image processing technique is known which gives an explanation in relation to the above-mentioned problem of the shift of the living body in a non-invasive living body measuring apparatus.

SUMMARY OF THE INVENTION

Thus, an object of the present invention is to provide a non-invasive living body measuring apparatus capable of measuring the same site on the same living body even if the positional relationship between the living body and the apparatus may vary.

The present invention provides a non-invasive living body measuring apparatus comprising: a light source section for irradiating a portion of a living body; an image capturing section for capturing an image of the irradiated portion of the living body; a data processing section for setting an analysis region in the captured image to obtain information on the living body and for extracting a characteristic pattern from the captured image; an output section for outputting the obtained information on the living body; and an operating section for operating at least one of the image capture, data processing and output sections, wherein when the image capturing section captures first and second images of a portion of a living body at different times and the data processing section extracts first and second characteristic patterns from the first and second images, respectively and set an analysis region in the first image, the data processing section sets an analysis region in the second image basing on a relative shift amount of the first and second characteristic patterns requisite for matching the first and second characteristic patterns to each other.

To explain it in more detail, it is assumed that a first captured image G1 and a second captured image G2 are given, where an analysis region A1 has been set on the first captured image G1 and an analysis region A2 has not been set on the second captured image yet. Characteristic patterns H1, H2 are extracted from the captured images G1, G2, respectively, and a relative shift amount Δ required in obtaining a good match of the characteristic patterns H1, H2 is determined. The position of the analysis region A2 on the captured second image G2 can be determined by using the position of the analysis region A1 on the first captured image G1 and the above-mentioned relative shift amountΔ.

In this manner, the same site of the living body may be set and measured as an analysis region on the different captured images obtained from the same living body, whereby the reproducibility of the information on the living body may be improved and the change of the information with time may be measured.

In another aspect, the present invention provides a non-invasive living body measuring method comprising the steps of: irradiating a portion of a living body with light; capturing an image of the irradiated portion of the living body; setting an analysis region in the captured image to obtain information on the living body and for extracting a characteristic pattern from the captured image; and outputting the obtained information on the living body; wherein when first and second images of a portion of a living body is captured at different times and first and second characteristic patterns are extracted from the first and second images, respectively and an analysis region in the first image is set, an analysis region in the second image is set basing on a relative shift amount of the first and second characteristic patterns requisite for matching the first and second characteristic patterns to each other.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Figure 1:
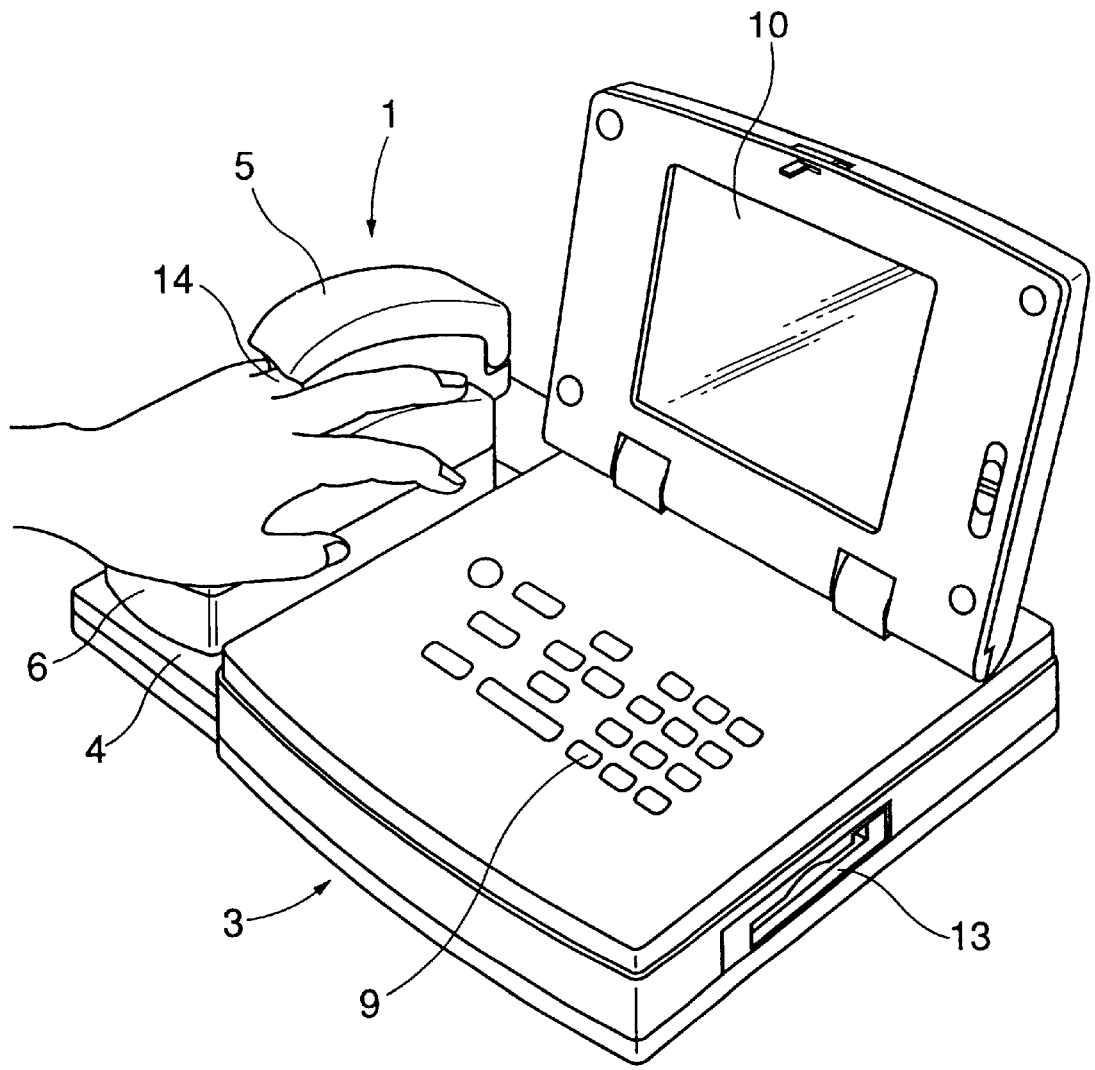
FIG. 1 is a perspective view showing an outlook of an embodiment of the present invention.

In a non-invasive living body measuring apparatus according to the present invention, a portion of a living body (suitably a mammal) is not a tissue separated from the living body but refers to a portion of a tissue as it is present in the living body and suitable for measurement. In the case of a human being, a finger, a thumb, or an ear lobe may be mentioned as an example of the portion of the living body. In the case of a rat or a mouse, a tail may be mentioned as an example for measurement. The information on the living body refers to information on the morphology (shape, size, or the number) of the living body tissues or information on the concentration of a living body component or the like. Specifically, the in formation on the living body may be, for example, the dimension of a blood vessel, the concentration of a blood component (such as hemoglobin or hematocrit), the concentration ratio of the blood components (such as an oxidation ratio of the blood), or the like.

In view of facility in operation and handling, it is preferable that the apparatus of the present invention separately includes a detecting section (detection unit, detecting device) for obtaining image information from the living body and an analyzing section (analysis unit, analyzing device) for analyzing the obtained image information. The two sections are connected by means of an information transmitting means such as a connector or a cable. The detecting section may include a light source section and an image capturing section, and the analyzing section may include a data processing section for analyzing the information on the living body, an output section, and an operating section.

The light source section may include a light source such as a semiconductor laser (LD), a LED, or a halogen lamp, whereby light beams from the light source is applied on the living body directly or via an optical fiber or the like. The light beams to be applied on the living body preferably have a wavelength within the range of 600 to 950 nm so that the light beams may be transmitted through the living body tissue and may not be absorbed so much by water.

The image capturing section may include an optical element such as a lens and an image capturing element such as a CCD. The image information from the living body is created by the image capturing element.

In order to obtain a more suitable image information, the detecting section preferably includes a holding member for holding the portion of the living body relative to the optical system. If the portion of the living body is, for example, a finger or a thumb of a hand of a human being, the holding member may be a member capable of holding the finger or the thumb detachably without pressing it between the light source section and the image capturing section. For example, it is possible to use a system in which the finger or the thumb is held between movable pieces.

The analyzing section maybe, for example, a microcomputer or a commercially available personal computer including a CPU, a ROM, a RAM, and an I/O port. The analyzing section may include a data processing section for analyzing the information on the living body from the captured image, an operating section for inputting various data and for performing various operations, and an output section for outputting results of analysis on the image information of the living body. The output section may be, for example, a display device such as a CRT or a liquid crystal display, or a printing device such as a printer. The operating section may be, for example, a key board, a ten key, a touch key, or the like.

The data processing section includes a function of extracting a characteristic pattern of a captured image and a function of setting an analysis region on a captured image, on which the analysis region has not been set yet, on the basis of a relative shift amount of the character patterns which is required in obtaining a good match between the characteristic patterns. This makes it possible to set an analysis region at the same site on a plurality of captured images obtained by rearrangement of the same living body with a predetermined time interval (including an interval of a predetermined number of days), thereby to measure the living body information in the analysis region. In other words, the same site may be measured with respect to different captured images obtained from the same living body, leading to improvement in the accuracy and the reproducibility of the living body information. Also, a change of the living body information with time (including the change with days) may be measured. If the analysis region is set on the same blood vessel site, it is possible to obtain a blood vessel dimension at the blood vessel site and the concentration of a blood cell component flowing through the blood vessel site as the living body information.

For determining the relative shift amount required in obtaining a good match between the characteristic patterns, it is preferable from a practical point of view to calculate an evaluation value representing a degree of coincidence of the characteristic patterns each time one of the characteristic patterns is moved (shifted) relative to the other of the characteristic patterns and to determine the relative shift amount based on the calculated evaluation value.

Here, if the degree of coincidence of the characteristic patterns remains below a predetermined level, it is preferable to issue a warning.

In order to more desirably extract a characteristic pattern from a captured image having a density blur, it is preferable that, for each object pixel constituting the captured image, an average density of a local region having a center at the object pixel is calculated and the characteristic pattern of the captured image is extracted by binarizing each object pixel using the average density.

Further, in view of simplifying and increasing the speed of the process, it is preferable to calculate an average density of a portion of the pixels selected from the local region to determine the average density of the local region.

Further, the characteristic pattern of the captured image may be a blood vessel pattern obtained by extracting a blood vessel portion. The blood vessel pattern may be obtained by observing the brightness of the pixels constituting the captured image and connecting each pixel having a lower brightness than the surrounding pixels.

EXAMPLES

Figure 2:
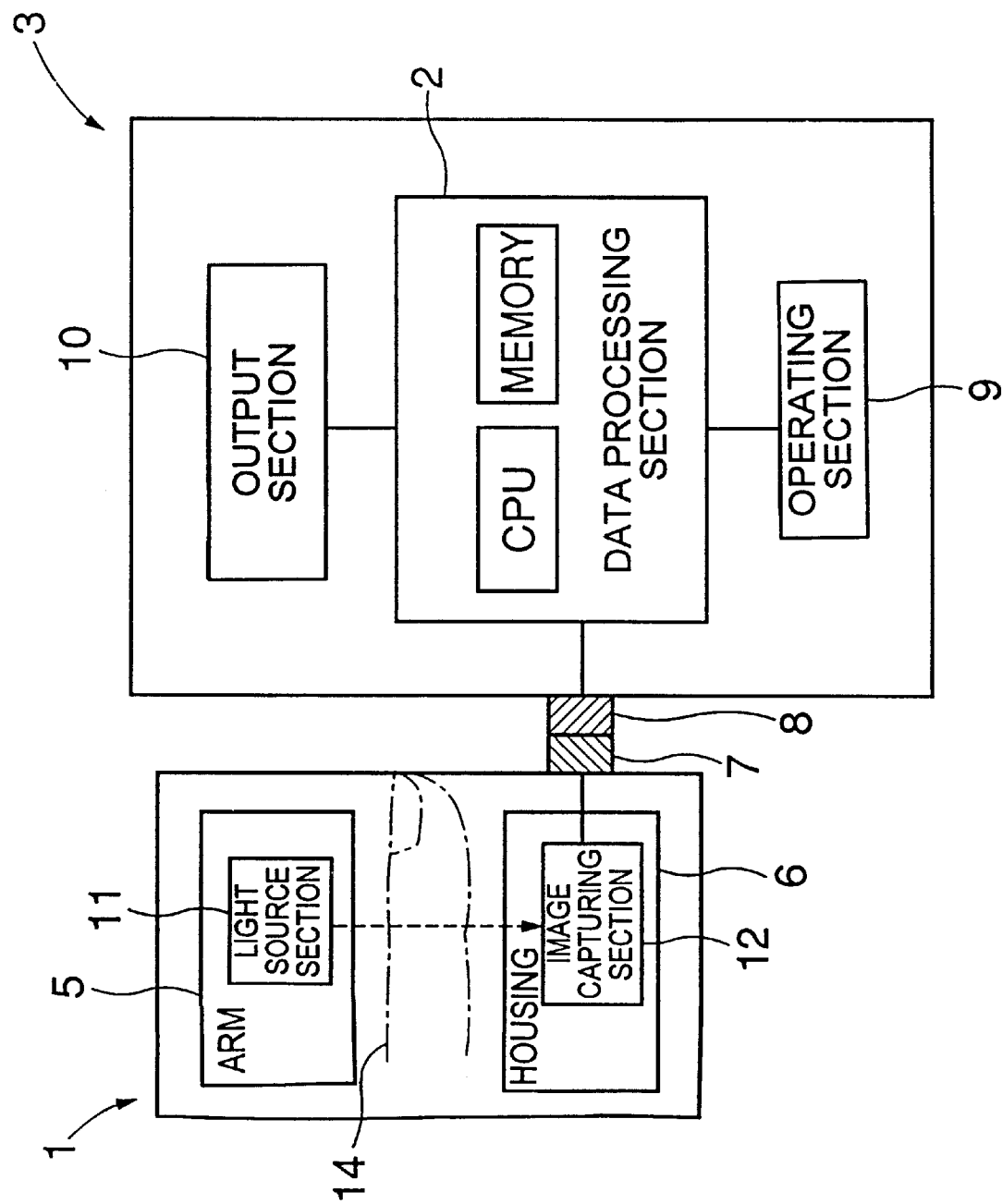
FIG. 2 is a block diagram of the embodiment of the present invention.

FIG. 1 is a view showing an outlook of one embodiment of a non-invasive living body measuring apparatus according to the present invention and shows a state in which a mouse-shaped detecting section 1 is mounted on a mounting section 4 of an analyzing section 3 having a shape like a notebook type personal computer. FIG. 2 is an overall block diagram functionally representing the non-invasive living body measuring apparatus of FIG. 1.

A detecting section 1 mounted on the mounting section 4 is electrically and mechanically connected to the analyzing section 3 by means of a connector 7 on the detecting section 1 side and a connector 8 on the analyzing section 3 side. In order to obtain freedom of measurement and handling, it is possible to detach the detecting section 1 from the mounting section 4 of the analyzing section 3 and to connect the detecting section 1 and the analyzing section 3 by means of a connecting cord with connectors.

The detecting section 1 includes an arm 5 and a housing 6 that can be rotated relative to the arm 5. A light source section 11 is incorporated in the inside of the arm 5, and an image capturing section 12 is incorporated in the inside of the housing 6 facing the arm 5. A human finger 14 is held between the arm 5 and the housing 6, and a light beam is applied to the dorsal side of the finger at the second joint portion of the finger 14 to capture a transmitted optical image through the ventral side of the finger. The finger is elastically held from both sides of the finger.

The light source section 11 includes a light emitting element having a plurality of LEDs with different wavelengths. L3989 (manufactured by Hamamatsu Photonics K.K.) having a center wavelength of 830 nm and a half value width of 40 nm is used as the first LED, and L25656 (manufactured by the same company) having a center wavelength of 890 nm and a half value width of 50 nm is used as the second LED. Only the first LED is energized in measuring the blood vessel width. On the other hand, both the first and second LEDs are energized in measuring the blood component concentration.

The analyzing section 3 includes a data processing section 2, an output section (liquid crystal monitor) 10, and an operating section (a plurality of keys) 9. An insertion hole 13 for a floppy disk serving as an external storage medium is disposed in the analyzing section 3 for external storage of measurement information and the like.

FIG. 2 is an overall block diagram of the non-invasive living body measuring apparatus according to this embodiment.

The data processing section 2 of the analyzing section 3 is a computer including a CPU and a memory. The data processing section 2 comprises a characteristics extracting function of creating a characteristic pattern of a captured image of the finger 14 obtained by the image capturing section 12 of the detecting section 1, a function of storing the characteristic pattern, a function of determining a relative shift amount of the characteristic patterns of different captured images which is required in obtaining a good matching of the characteristic patterns, an analysis region setting function for setting the same blood vessel site as an analysis region with respect to the captured image on the basis of the relative shift amount, a density profile extracting function of extracting a density distribution of a blood vessel portion in the analysis region as a density profile, a quantitating function of quantitating a morphological feature of the extracted density profile, a calculating function of calculating living body information on a blood vessel dimension, a blood component concentration, or the like based on the quantitated feature, and the like.

Figure 4:
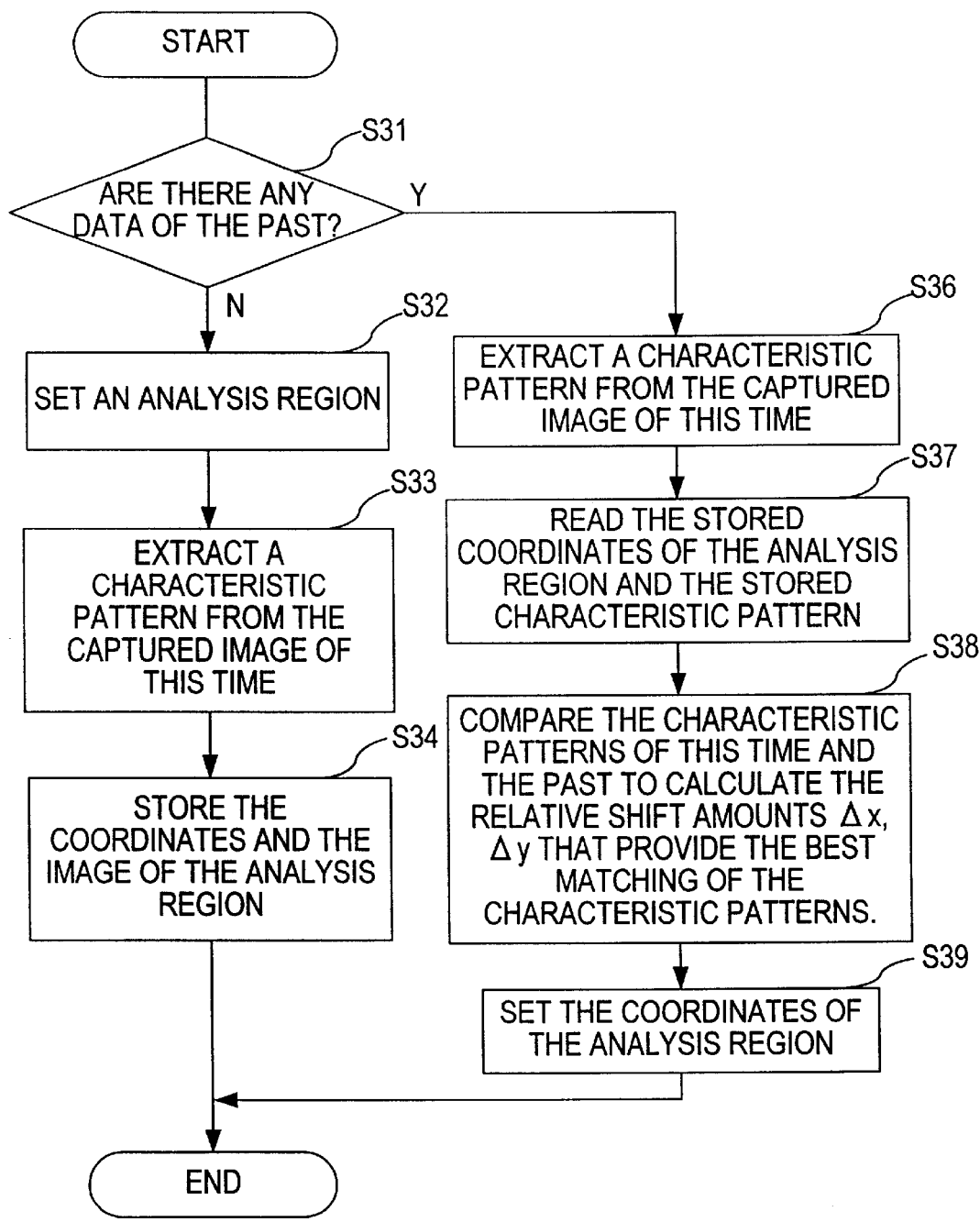
FIG. 4 is a flow chart showing an operation of the embodiment of the present invention.
Figure 5:
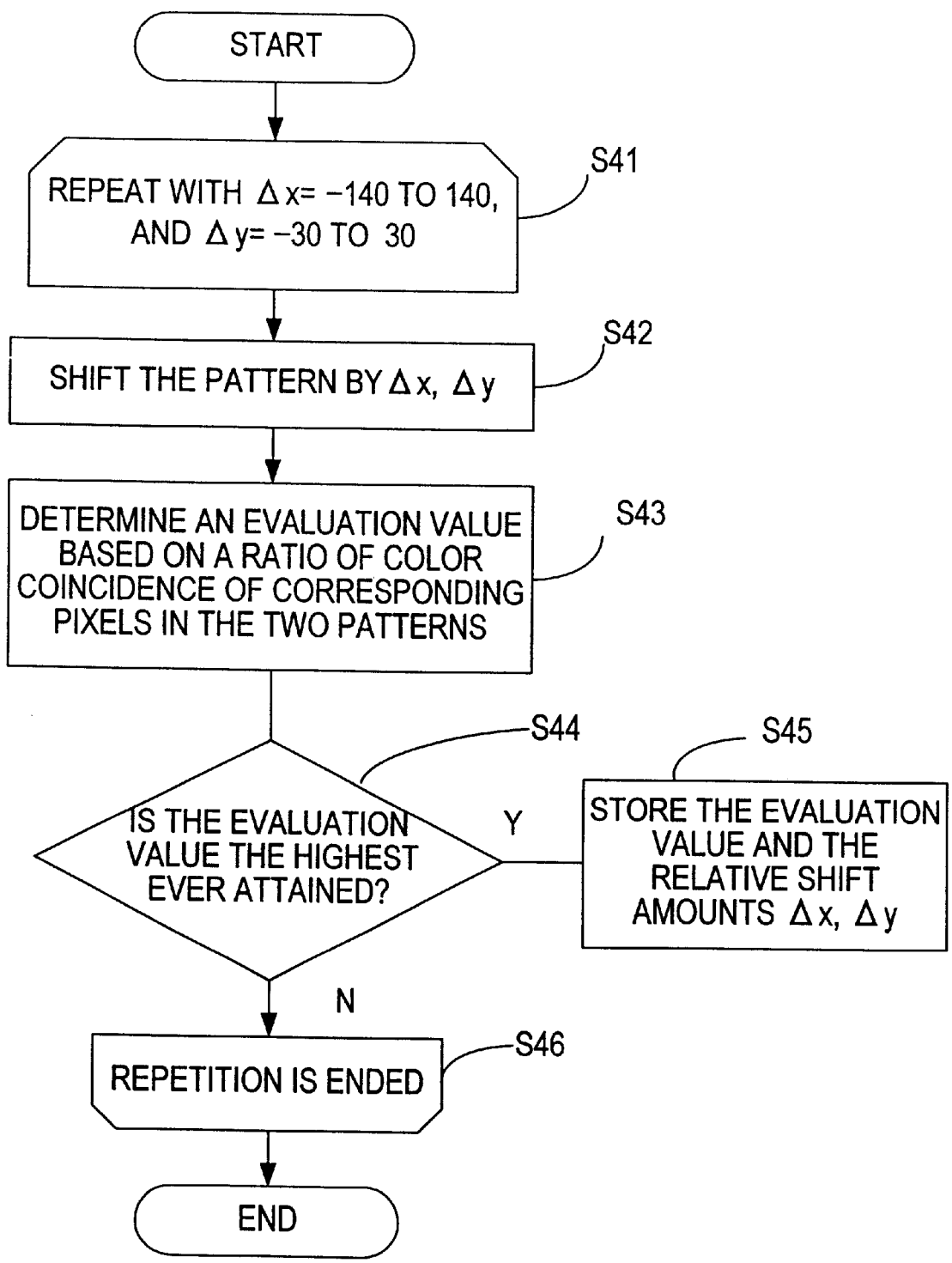
FIG. 5 is a flow chart showing an operation of the embodiment of the present invention.

With reference to flowcharts shown in FIGS. 3, 4, and 5, an explanation will be given on a concrete procedure of measuring the blood vessel width. FIGS. 4 and 5 are flowcharts for setting the analysis region and for calculating the relative shift amount, respectively. Here, an image of a finger of the same person is captured time-sequentially (in time series) for a plurality of times using one wavelength to measure the time-sequential change of the blood vessel width at the same blood vessel site.

First, the finger 14 is irradiated by means of the first LED (first wavelength) for image capturing, thereby to obtain an image (640 pixels in the x-direction×480 pixels in the y-direction) including a blood vessel (vein) image that is present on a skin surface of the finger 14 (step S1).

In this apparatus, a file is stored for each person to be inspected. If measurements were not performed in the past on the person to be inspected (that is, no stored file is present or no corresponding data is present even though a stored file is present), it is assumed that the current measurement is the first measurement (step S31). In this case, a region including a blood vessel image of the best contrast is searched for from the captured image G1 (x, y), and the region including the blood vessel image is set as an analysis region A1 (x, y) (step S32). The analysis region A1 (x, y) is usually set automatically. However, a user may operate the operating section 9 to manually set the analysis region A1 (x, y) by observing a monitored image displayed on the output section 10.

Next, a characteristic pattern of the captured image G1 (x, y) is extracted (step S33), and the extracted characteristic pattern is stored into a memory. The positional information of the analysis region A1 (x, y) including the coordinates (p1, p2), (q1, q2), (r1, r2), and (s1, s2) of the four apexes of a quadrangle constituting the regional boundary of the analysis region A1 (x, y) is also stored into the memory (step S34). Then, if the current measurement is the first measurement for the person to be inspected, the procedure is ended.

Here, the image is binarized for extracting a characteristic pattern of the image. However, if the image is binarized using a constant threshold value, it is not possible to obtain good characteristics of the image, because the captured image G1 (x, y) may have a large density blur due to non-uniformity of radiation or difference in the thickness or the property of the living body.

Figure 10:
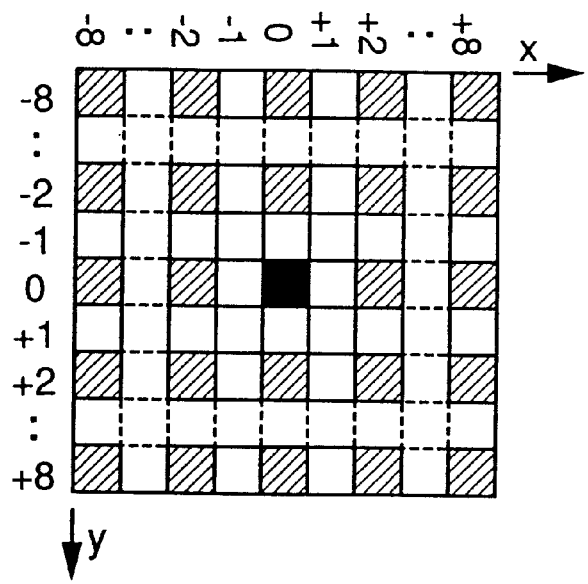
FIG. 10 is an explanatory view showing a target pixel and a local region.

Accordingly, a two-dimensional characteristic pattern of the image is extracted by setting a different threshold value for each pixel in the image. Namely, for each object pixel (x, y) (shown in solid black), a local region D (x, y) having a center at the object pixel (x, y) is set, as shown in FIG. 10, and the threshold value of the object pixel (x, y) is set to be an average density Dxy of the local region D (x, y). In this embodiment, the local region D (x, y) is assumed to be a region with 17 pixels×17 pixels and the average density of the local region D (x, y) is set to be an average density of 81 pixels (shown in gray) including the object pixel, which have been selected from the local region D (x, y) in a checkered configuration (i.e., every other pixel is selected) for performing a higher-speed operation. The selected pixels can be represented by $\{(x-i, y-j) | i, j=0, \pm 2, \pm 4, \pm 6, \pm 8\}$. In this embodiment, 9 pixels×9 pixels to 33 pixels×33 pixels are found to be suitable for the local region.

Figure 8:
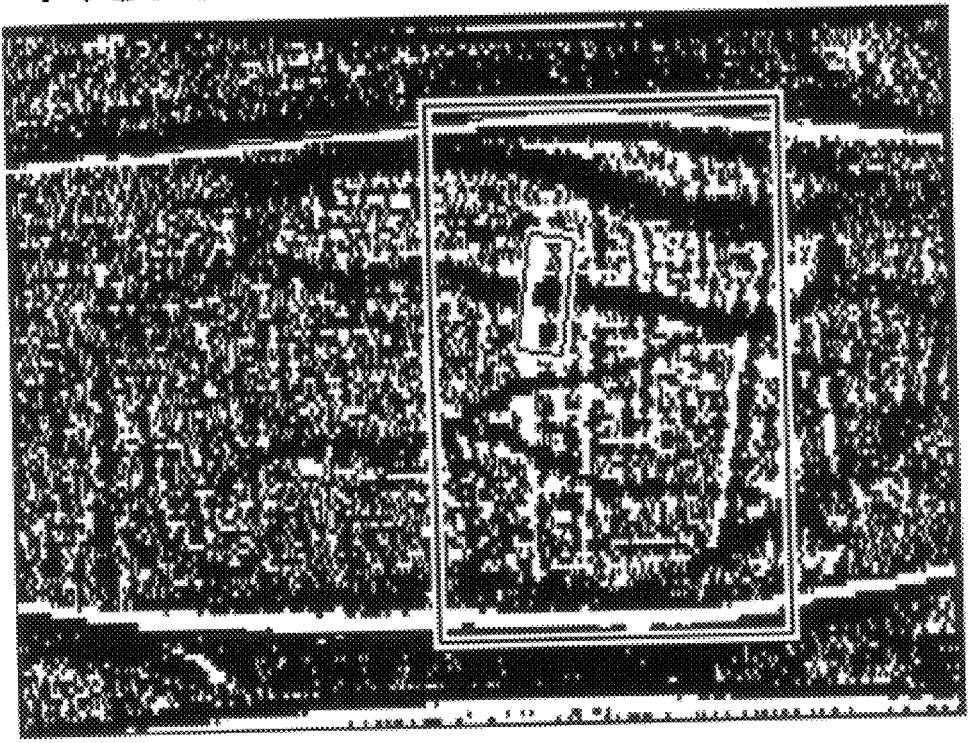
FIG. 8 is a characteristic pattern of the image of FIG. 6.

A good characteristic pattern representing the characteristics of the captured image G1 (x, y) such as shown in FIG. 8 is obtained by comparing the density of each object pixel (x, y) and the corresponding threshold value Dxy. This characteristic pattern illustrates the morphological features of blood vessels, wrinkles of the finger, and the like well. Here, it is to be noted that the region with 240 pixels in the x-direction×260 pixels in the y-direction located in the vicinity of the center of brightness is stored as the characteristic pattern H1 (x, y) instead of the whole region with 640 pixels×480 pixels. This contributes to achieving a higher speed process. A larger rectangle shown in FIG. 8 represents the characteristic pattern H1 (x, y), and a smaller rectangle shown in FIG. 8 represents the analysis region A1 (x, y) set in the characteristic pattern H1 (x, y).

Here, it is assumed that the vicinity of the center of brightness is a designated region having a center at the center of gravity of brightness. The center of gravity of brightness can be calculated by the following two formulas 1 and 2, and is represented by $(X_G, Y_G)$.

$$X_G = \sum_x \sum_y G(x, y) \cdot x \Big/ \sum_x \sum_y G(x, y) \quad (1)$$

$$Y_G = \sum_x \sum_y G(x, y) \cdot y \Big/ \sum_x \sum_y G(x, y) \quad (2)$$

Figure 6:
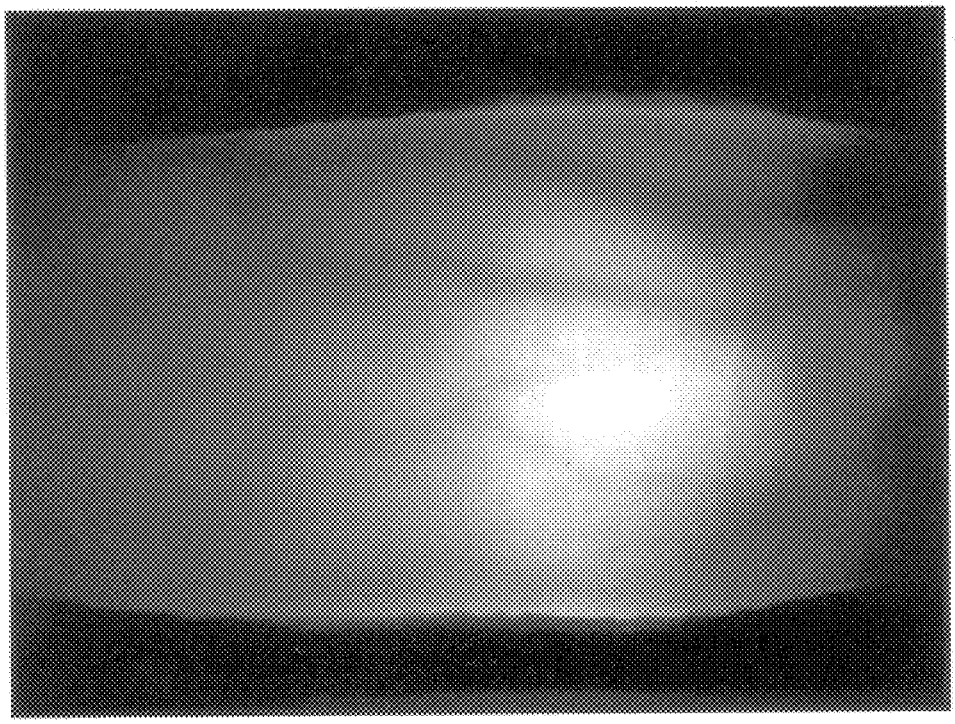
FIG. 6 is an example of an image obtained by the embodiment of the present invention.
Figure 7:
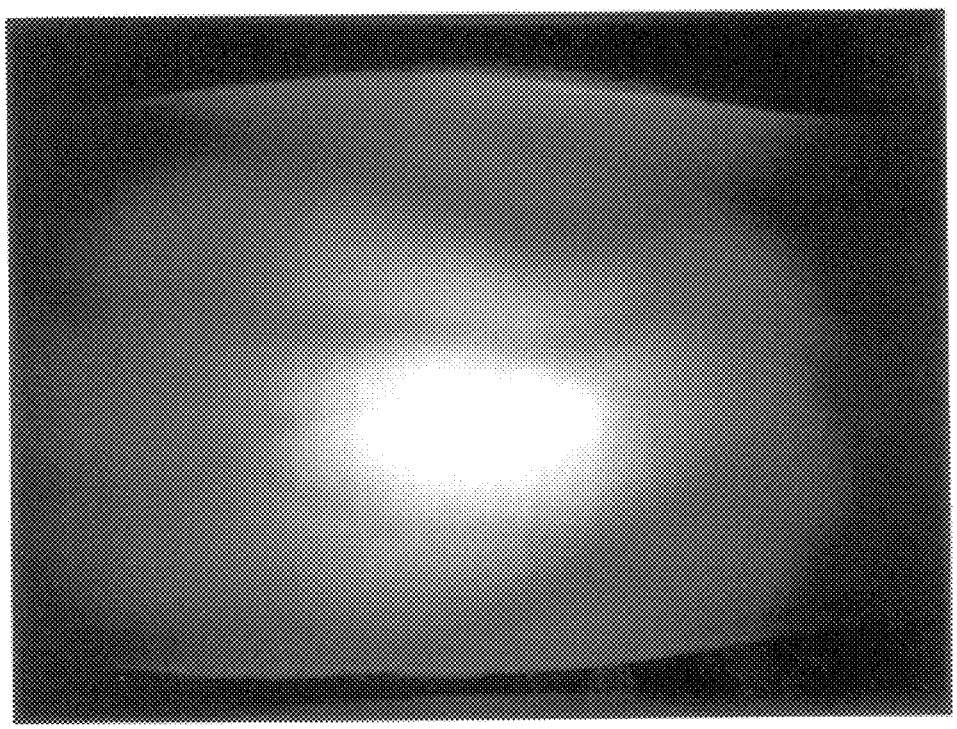
FIG. 7 is an example of an image obtained by the embodiment of the present invention.
Figure 9:
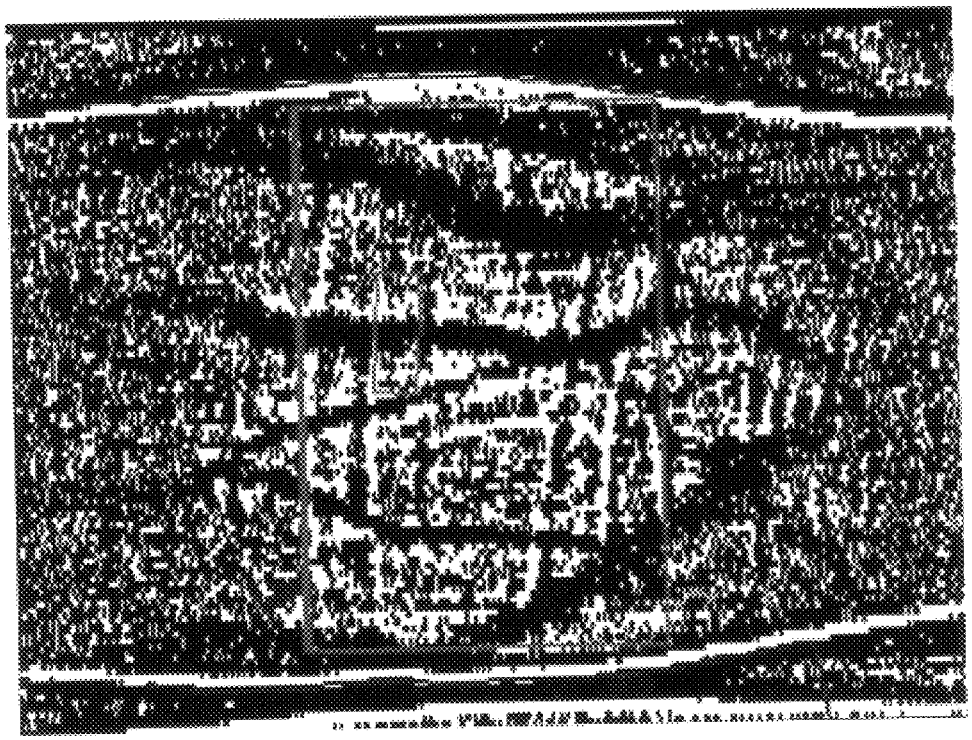
FIG. 9 is a characteristic pattern of the image of FIG. 7.

Now, if the current measurement is the second measurement for the person to be inspected (step S31) and a captured image G2 (x, y) such as shown in FIG. 7 is obtained (step S1), then a characteristic pattern H2 (x, y) with 640 pixels in the x-direction×480 pixels in the y-direction is obtained, as shown in FIG. 9, in the same manner as described above (step S36). Here, FIG. 7 is an image obtained in the case where the finger is a little shifted towards the left side as compared with FIG. 6.

Figure 11:
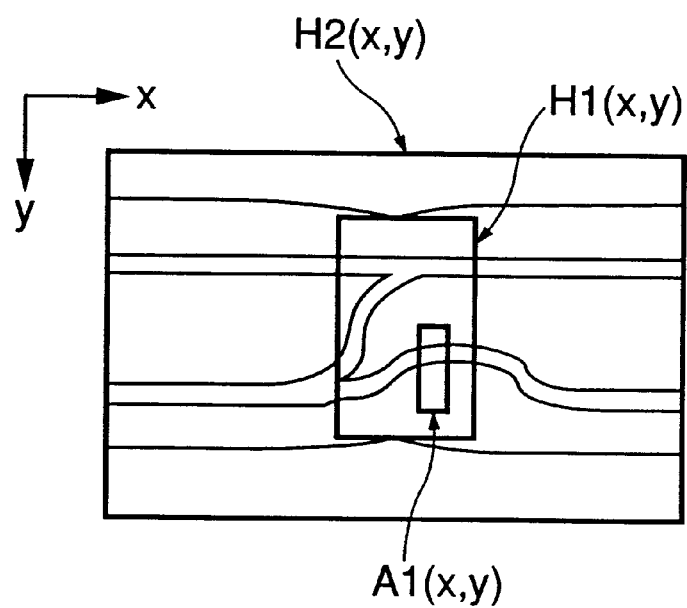
FIG. 11 is an explanatory view showing comparison of characteristic patterns.

Next, the above-mentioned first characteristic pattern H1 (x, y) is readout from the memory (step S37), and is compared with the second characteristic pattern H2 (x, y), as shown in FIG. 11, to determine a relative shift amount required in obtaining a good matching of the two characteristic patterns (step S38). Specifically, the first characteristic pattern H1 (x, y) is moved relative to the second pattern H2 (x, y) to determine the relative shift amount Δx, Δy that achieves a good matching of the two characteristic patterns. Then, the position of the analysis region A2 (x, y) in the second captured image G2 (x, y) is determined based on the position of the analysis region A1 (x, y) in the first captured image G1 (x, y) and the above-mentioned relative shift amount Δx, Δy.

With reference to FIG. 5, a concrete explanation will be given on the comparison between the two characteristic patterns H1 (x, y) and H2 (x, y).

The first characteristic pattern H1 (x, y) is moved by Δx in the x-direction and by Δy in the y-direction relative to the second characteristic pattern H2 (x, y) (step S42) to calculate an evaluation value EΔxΔy that reflects the degree of coincidence of the two characteristic patterns at that time (step S43). Here, the evaluation value EΔxΔy is the number of pixels in which the two corresponding pixels on the two characteristic patterns have the same value as determined by examining the value (0 or 1) of each pixel on each characteristic pattern. The evaluation value EΔxΔy is calculated each time the relative shift amount is changed within a predetermined range (steps S41, S46), and the shift amount Δx in the x-direction and the shift amount Δy in the y-direction that achieve the maximum evaluation value EΔxΔy is stored in the memory (steps S44, S45). Here, since the finger tends to be positioned by being shifted in the axis direction of the finger (x-direction), it is preferable to repeat the above-mentioned calculation of the evaluation value EΔxΔy by relatively moving the characteristic pattern at an interval of several pixels (for example, by every two to three pixels), in the x-direction. This contributes to achieving a higher speed operation.

Figure 21:
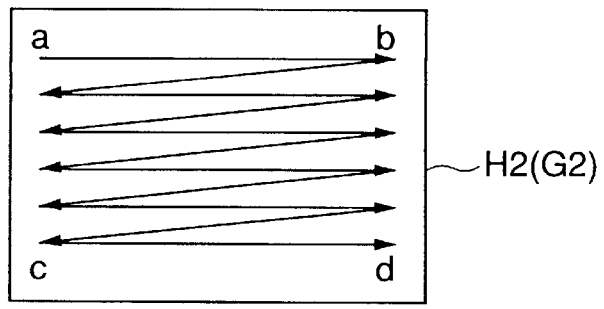
FIG. 21 is an explanatory view showing a method of moving the characteristic patterns according to the present invention.
Figure 22:
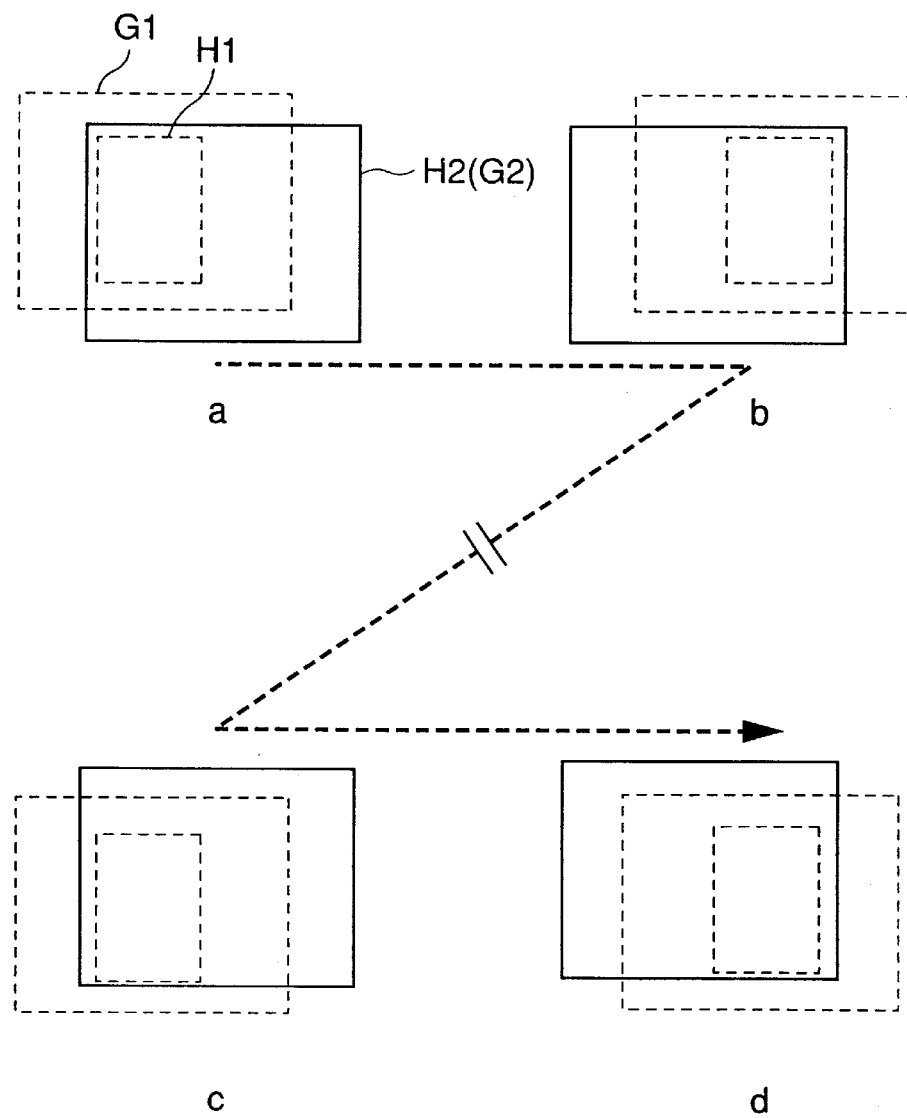
FIG. 22 is an explanatory view showing a method of moving the characteristic patterns according to the present invention.

Here, with reference to FIGS. 21 and 22, a detailed explanation will be give on a method of moving the first characteristic pattern H1 (x, y) relative to the second characteristic pattern H2 (x, y) by Δx in the x-direction and by Δy in the y-direction.

The first characteristic pattern H1 (x, y) is moved relative to the second characteristic pattern H2 (x, y) as shown in FIG. 21. The state shown by (a) in FIG. 22 is set to be a starting point. This corresponds to the position at which the first characteristic pattern H1 (x, y) is moved by Δx=−140 in the x-direction and Δy=−30 in the y-direction. Then, the characteristic pattern is shifted to the right by every several pixels, for example, by every two to three pixels, in the x-direction, until the characteristic pattern H1 (x, y) is moved by Δx=140 in the x-direction and Δy=−30 in the y-direction (the state shown by (b) in FIG. 22). Then, the characteristic pattern H1 (x, y) is moved back to the position shown by Δx=−140 in the x-direction and moved downwards by several pixels in the y-direction. Thereafter, the characteristic pattern H1 (x, y) is moved to the right in the x-direction by every several pixels again. This process is repeated until the characteristic pattern H1 (x, y) is moved by Δx=−140 in the x-direction and Δy=30 in the y-direction (the position shown by (c)). Finally, the characteristic pattern H1 (x, y) is moved to the position shown by (d), i.e. the position at which the characteristic pattern H1 (x, y) is moved by Δx=140 in the x-direction and Δy=30 in the y-direction. In this manner, the first characteristic pattern H1 (x, y) is moved relative to the second characteristic pattern H2 (x, y) by every several pixels, and the evaluation value $E\Delta x\Delta y$ is calculated every time the characteristic pattern is moved. The relative shift amount required in obtaining a good matching of the characteristic patterns may be determined by finding a relative shift amount $\Delta x$, $\Delta y$ that achieves the maximum evaluation value $E\Delta x\Delta y$.

In this Example, the relative shift amount was $\Delta x=63$ and $\Delta y=-7$, and the degree of coincidence at that time was 62.1%. Here, the degree of coincidence as used herein represents a ratio of the evaluation value obtained when one characteristic pattern is moved by a predetermined amount relative to the other characteristic pattern, as divided by the evaluation value obtained if the two characteristic patterns match with each other completely.

As a result of the above process, the coordinates of the apexes P', Q', R', S' of the analysis region A2 (x, y) in the second captured image G2 (x, y), where an analysis region has not been set yet, may be determined as (p1+$\Delta x$, q1+$\Delta y$), (p2+$\Delta x$, q2+$\Delta y$), (p3+$\Delta x$, q3+$\Delta y$), (p4+$\Delta x$, q4+$\Delta y$), respectively (step S39). In this manner, the same blood vessel site as has been set in the first captured image G1 (x, y) can be set as an analysis region in the second captured image G2 (x, y) Even if an image of a finger of a person to be inspected is captured for n times in time series (for example, by every two hours), the same blood vessel site can always be set as analysis regions A1, A2, . . . , An, though the relative position of the captured image may be different each time the image is captured.

Figure 3:
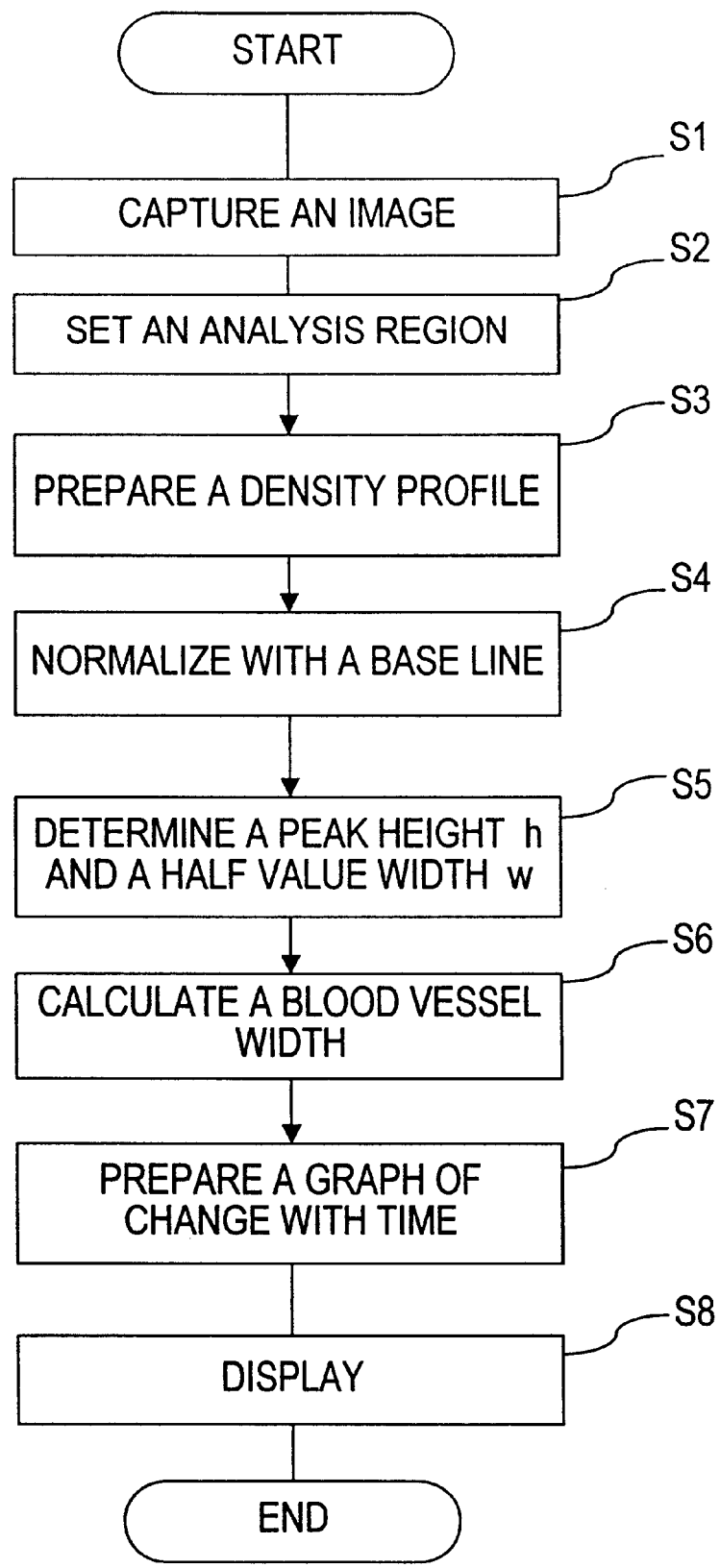
FIG. 3 is a flow chart showing an operation of the embodiment of the present invention.
Figure 12:
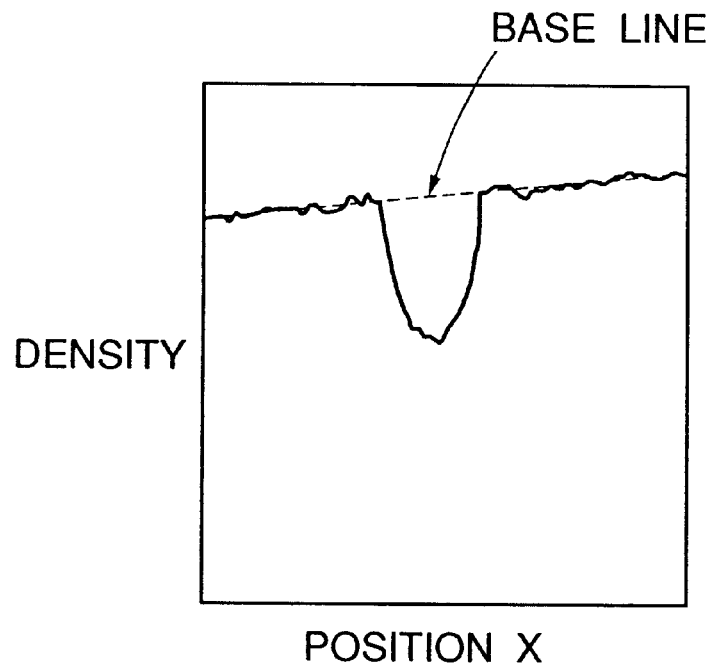
FIG. 12 is an explanatory view showing a concentration profile.
Figure 13:
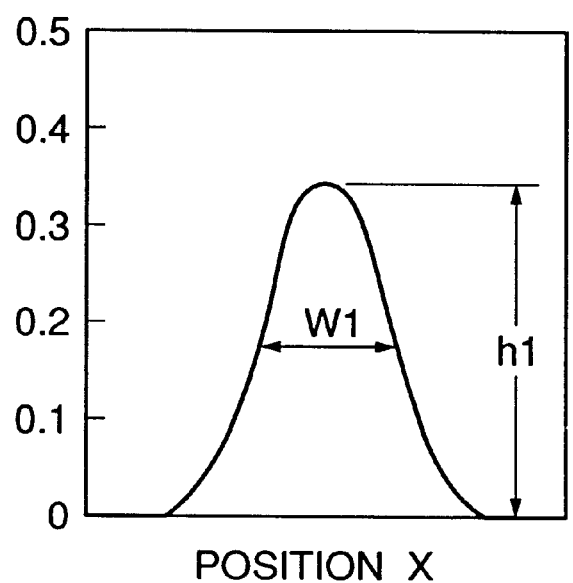
FIG. 13 is an explanatory view showing a normalized concentration profile.

Next, in the step S3 shown in FIG. 3, a density profile (FIG. 12) along the direction perpendicular to the blood vessel is prepared in the set analysis region, and the density profile is normalized using a base line to give a normalized density profile which is not dependent on the amount of incident light, as shown in FIG. 13 (step S4).

A peak height h1 and a distribution width (half value width) w1 at (½)h1, which are morphological features of the normalized density profile (FIG. 13), are calculated (step S5), whereby information on the living body is obtained and stored in the memory. Here, the calculated half value width w1 is assumed to be representing the blood vessel width (step S6).

When the measurement is completed, a graph or a table representing a time-sequential change of the calculated blood vessel width is created and displayed (steps S7, S8).

The above is an example of measurement of the blood vessel width by using one wavelength. However, if a plurality of wavelengths are used, a hemoglobin concentration can be measured. In other words, the hemoglobin concentration can be calculated on the basis of the morphology of a normalized density profile obtained for each wavelength. For the details of this measurement, reference is made to Published International Patent Application No. WO97/24066, so that an explanation thereof is omitted here.

Figure 14:
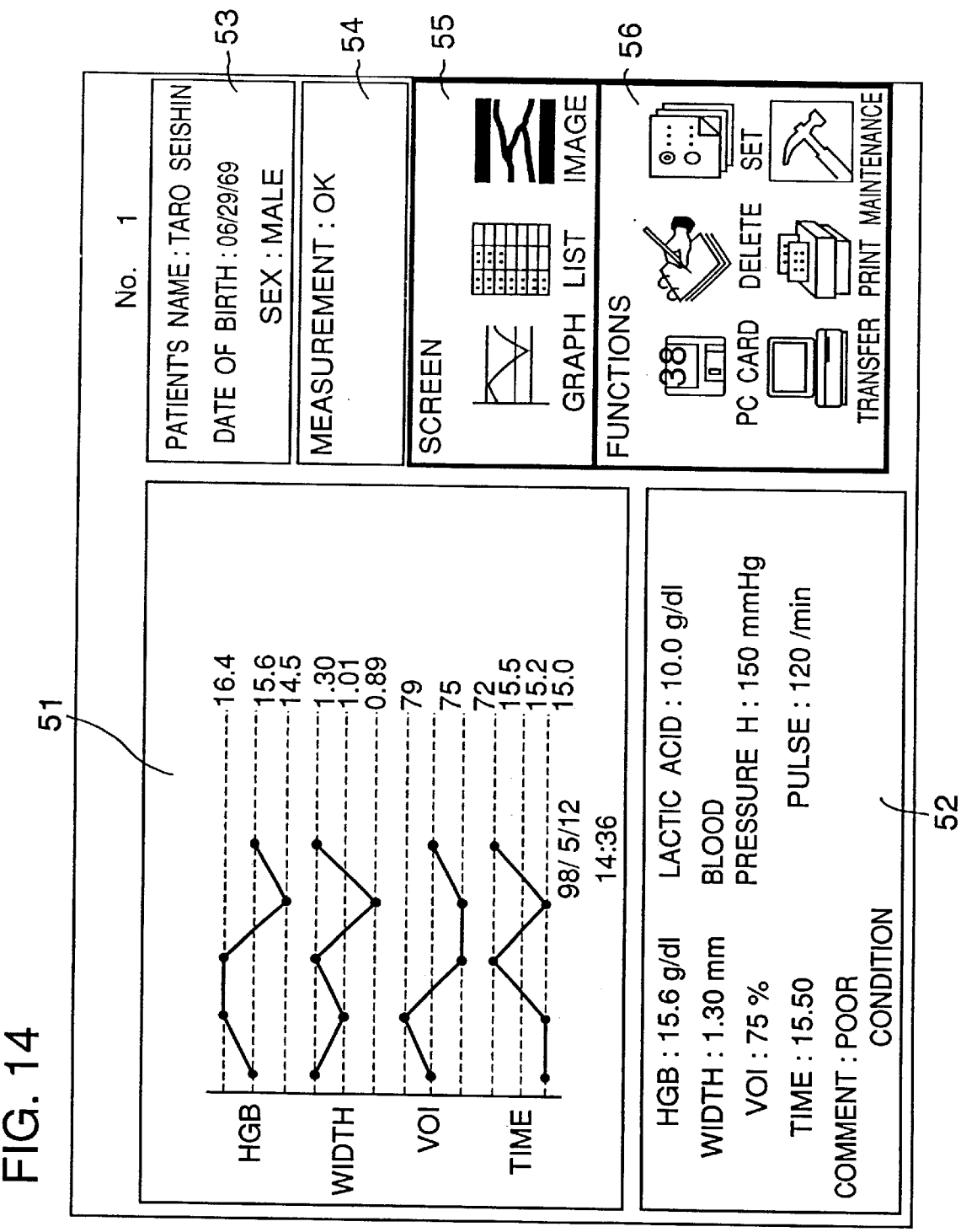
FIG. 14 is an explanatory view showing a display example according to the present invention.

FIG. 14 is a display example of an output section 10 (liquid crystal display). The display screen includes a graph displaying area 51, a measurement data displaying area 52, a measurement information area 53, a message area 54, a data display form switching area 55, and a command area 56.

The graph displaying area 51 displays the hemoglobin concentration HGB and the blood vessel width, which are the measured living body information, as graphs in time series.

The measured data displaying area 52 displays the measured data at the time of measurement on the above-mentioned graph. The measured information area 53 displays the measured person's data such as the measurement number, the measured person's name, the year and date of birth, the sex, and the like. The message area 54 displays a message showing a system state or a message for prompting an action of the person to be measured.

The data displaying form switching area 55 displays an icon for switching the data display form (graph, data list, captured image) If the captured image is to be displayed, it is preferable to show the analysis region as well.

The command area 56 displays icons for executing various commands. Selection of icons allows execution of various operations such as recordation of the measured data into a PC card, setting the deletion of a file, a transfer of the data, printing, the maintenance, and the like.

The graphs shown in the graph displaying area 51 of FIG. 14 are time-sequential graphs showing the blood vessel width, the hemoglobin concentration HGB, the oxidation ratio VOI, which have been measured before an everyday exercise, and a score of time trial separately input (data is input for each measurement) . Also, a bar (shown in broken lines) indicating the measurement point on the time-sequential graph can be moved by means of a "cursor" key, and the corresponding date of measurement, measurement time, measurement result, comments, and the like can be displayed on the display area 52.

Next, an explanation will be given on an example in which a characteristic pattern different from the previously explained characteristic pattern is used.

First, a bent line (a series of connected line segments) connecting the "valley" points having a lower brightness value than the surrounding points (i.e. the blood vessel pattern) is extracted and recorded as a characteristic pattern of an image.

Figure 15A:
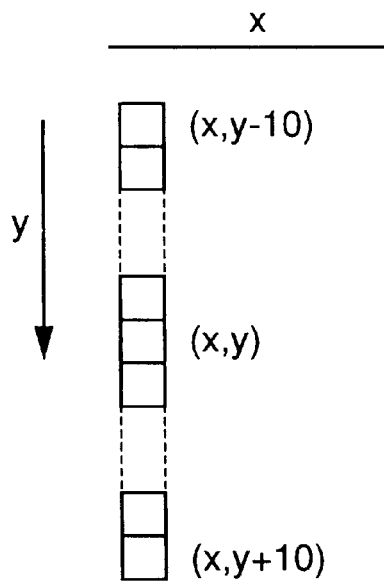
FIGS. 15(A) and 15(B) are explanatory views showing a method of obtaining a blood vessel pattern according to the present invention.

In other words, with respect to an object pixel (x, y) shown in FIG. 15(A), the points having a brightness value lower than 95% of the average brightness value within the range of ±10 pixels of the object pixel, i.e. within the range of (x, y−10) to (x, y+10), are extracted as blood vessel candidate points. In other words, the pixels whose brightness value is lower than 95% of the average brightness value in the group of sequential 21 pixels in the y-direction are selected as the blood vessel candidate points. Then, the pixel group is shifted by one pixel each time in the y-direction to extract the blood vessel candidate points from one end to the other end in the y-direction. Next, the group is shifted by one pixel in the x-direction, and the above operation is repeated to extract the blood vessel candidate points in the whole region of the captured image G1 (x, y).

Figure 15B:
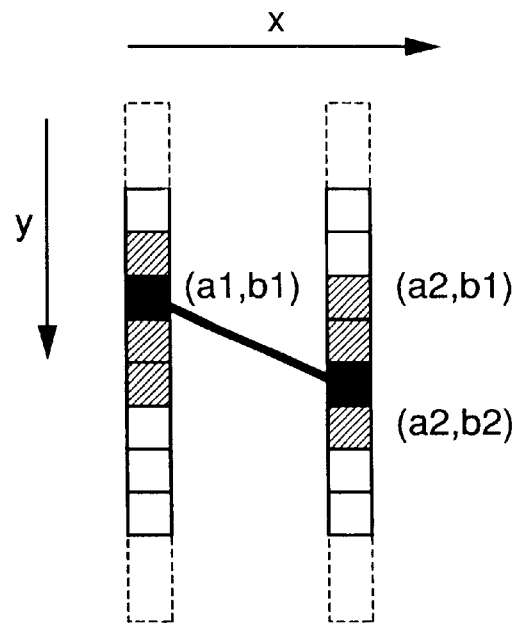

Next, referring to FIG. 15(B), the blood vessel candidate point having the lowest brightness value within the range of ±10 pixels, i.e. the lowest brightness point (a1, b1) (shown in solid black), is extracted. Here, the hatched portions indicate the blood vessel candidate points. Then, in an adjacent column, the lowest brightness point (a2, b2) (shown in solid black) is extracted within the range of ±10 pixels with respect to the point (a2, b1) corresponding to the lowest brightness point (a1, b1) . Then, the lowest brightness point (a1, b1) and the lowest brightness point (a2, b2) are connected. The above-mentioned operation is repeated for the whole region in the captured image G1 (x, y) to form a blood vessel pattern.

Figure 18:
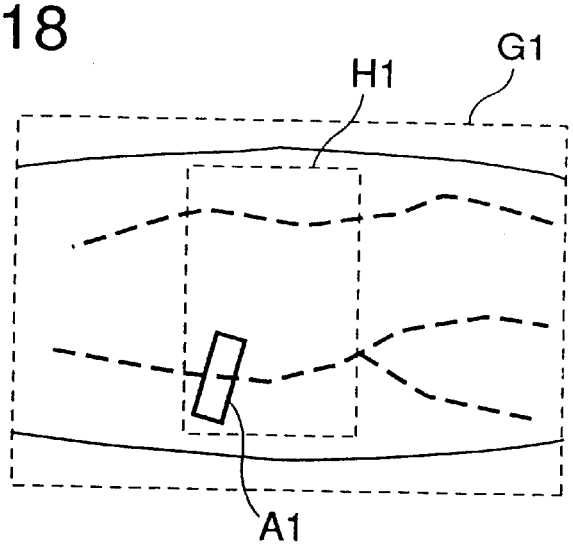
FIG. 18 is a view showing a characteristic pattern of an image captured at the first time.

Thus, the captured image G1 (x, y) is represented by the blood vessel pattern shown by a thick broken line in FIG. 18. With respect to a characteristic pattern in the captured image G1 (x, y), a region near the center of brightness is stored in the memory as a characteristic pattern H1 (x, y) in the same manner as in the first embodiment. Referring to FIG. 18, the characteristic pattern H1 (x, y) is shown by a larger rectangular broken line, and an analysis region A1 (x, y) set in the characteristic pattern H1 (x, y) is shown by a smaller rectangular broken line.

Figure 19:
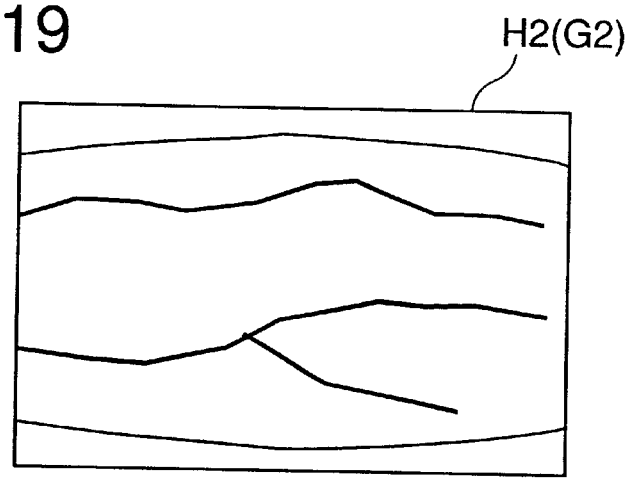
FIG. 19 is a view showing a characteristic pattern of an image captured at the second time.

Regarding a captured image G2 (x, y) obtained by the second measurement, a characteristic pattern H2 (x, y) with 640 pixels in the x-direction and 480 pixels in the y-direction is obtained, as shown in FIG. 19, in the same manner as mentioned above.

Figure 16:
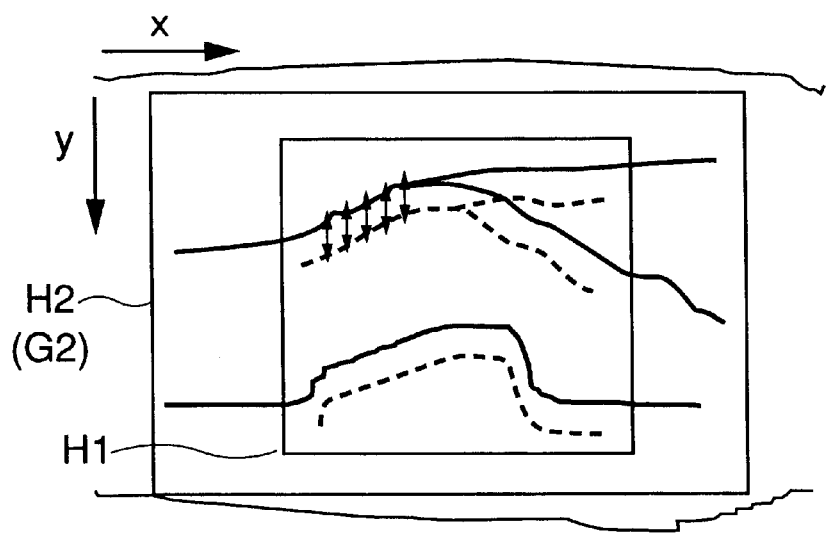
FIG. 16 is an explanatory view showing a method of obtaining an evaluation value according to the embodiment of the present invention.
Figure 17:
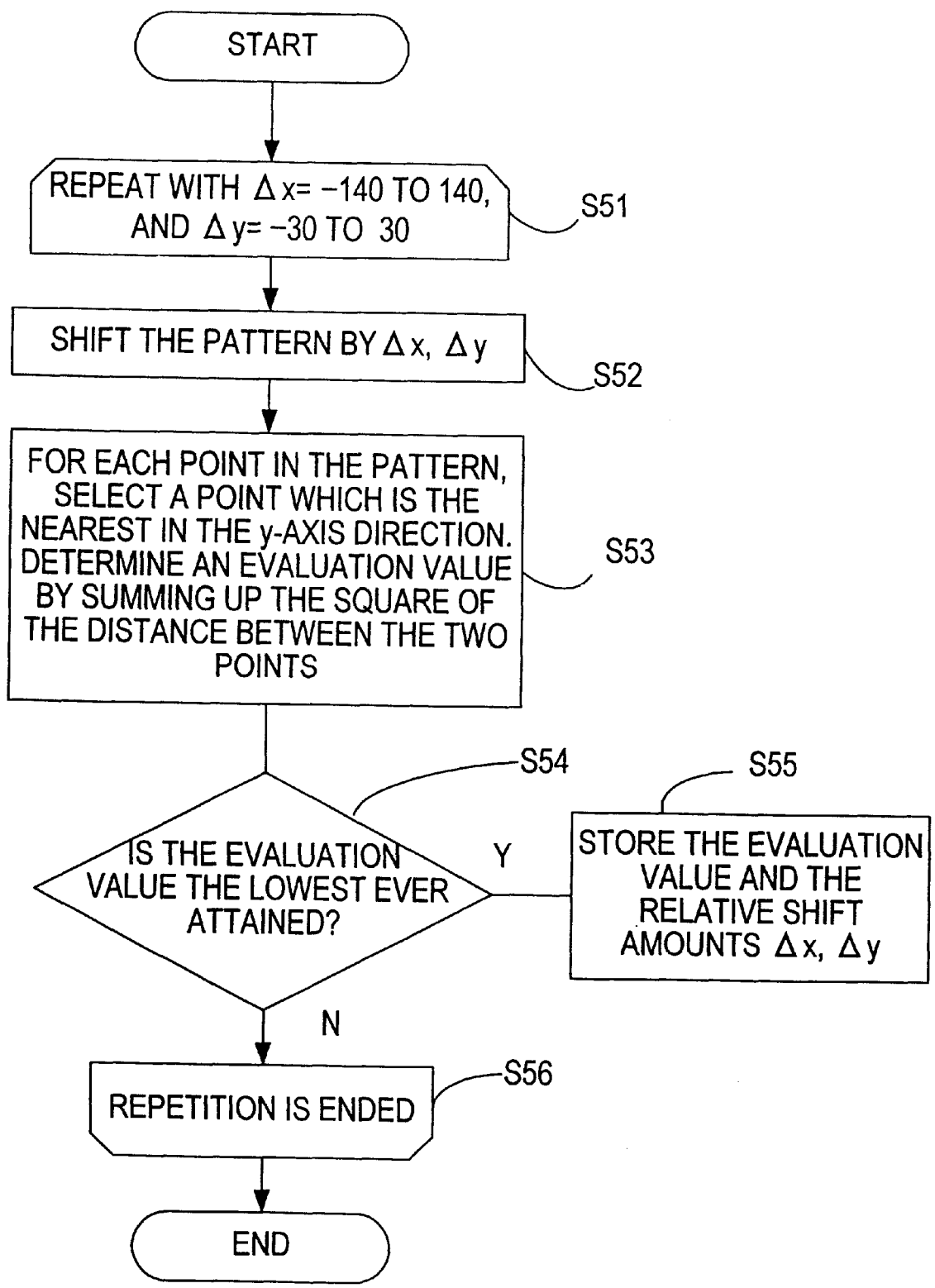
FIG. 17 is a flowchart showing an operation of the embodiment of the present invention.

Next, with reference to FIGS. 16 and 17, comparison of the characteristic patterns H1 (x, y) and H2 (x, y) will be specifically explained.

The first characteristic pattern H1 (x, y) is moved relative to the second characteristic pattern H2 (x, y) by $\Delta x$ in the x-direction and $\Delta y$ in the y-direction to calculate an evaluation value $F\Delta x \Delta y$ reflecting a degree of coincidence of the two patterns (steps S52, S53). Referring to FIG. 16, a distance between a point on the blood vessel pattern of H1 (x, y) and a point on the blood vessel pattern of H2 (x, y) in the y-direction is examined, and the square of the shortest distance between the points that give the shortest distance is calculated. The evaluation value $F\Delta x \Delta y$ is obtained by determining and summing up the square of the shortest distances of all the points in the pattern (i.e. the distances shown by the arrows in FIG. 16). This procedure is repeated by changing the relative shift amount within a predetermined range to calculate the evaluation value $F\Delta x \Delta y$ (steps S51, S56). The shift amount $\Delta x$ in the x-direction and the shift amount $\Delta y$ in the y-direction that provide the smallest evaluation value $F\Delta x \Delta y$ is stored in the memory (steps S54, S55).

Figure 20:
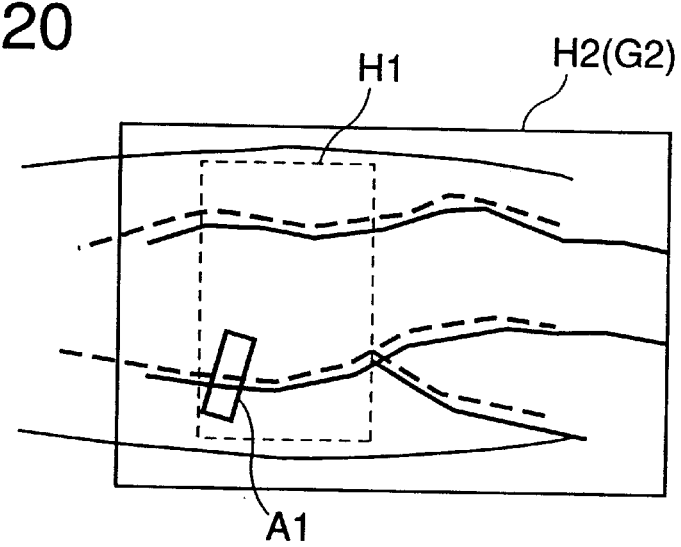
FIG. 20 is a view showing matched characteristic patterns according to the present invention.

In this manner, the position that provides the best matching of the first characteristic pattern H1 (x, y) and the second characteristic pattern H2 (x, y) is obtained (FIG. 20).

As shown and described above, according to the present invention, a characteristic pattern is extracted for each captured image and, by using a relative shift amount that is required in obtaining a good matching of the two patterns, an analysis region can be set on the same site of the living body in the captured image where the analysis region has not been set yet. Since an analysis region can be set on the same site of the living body in different captured images for measurement, the reproducibility of the measurement of the living body information can be improved and the time-sequential change of the living body information can be measured.

It is preferable from a practical point of view if the relative shift amount required in obtaining a good matching of the characteristic patterns is determined by calculating an evaluation value representing a degree of coincidence of the two characteristic patterns each time one of the characteristic patterns is moved relative to the other of the characteristic patterns and determining the relative shift amount based on the calculated evaluation value.

If, for each object pixel, an average density of a local region having a center at the object pixel is calculated and each object pixel is binarized using the average density in obtaining the characteristic patterns, the characteristics of the captured image G1 (x, y) can be obtained well even if the captured image has a density blur.

Further, since the characteristic pattern of the captured image is a blood vessel pattern obtained by observing the brightness of the pixels constituting the captured image and connecting the points having a lower brightness value that the surrounding pixels, the comparison of the characteristic patterns can be carried out at a higher speed because the number of pixels in the captured image G1 (x, y) is small.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

I claim:

1. A non-invasive living body measuring apparatus comprising:

a light source section for irradiating a portion of a living body;

an image capturing section for capturing an image of the irradiated portion of the living body;

a data processing section for setting an analysis region in the captured image to obtain information on the living body and for extracting a characteristic pattern from the captured image;

an output section for outputting the obtained information on the living body; and an operating section for operating at least one of the image capture, data processing and output sections, wherein when the image capturing section captures images of a portion of a living body a plurality of times and the data processing section extracts a characteristic pattern from a first image, sets an analysis region in the first image, and then sets an analysis region in a subsequent image based on a relative position of the characteristic pattern in the subsequent image as determined by pattern matching within the subsequent image.

2. The non-invasive living body measuring apparatus of claim 1, wherein the data processing section determines the relative shift amount of the analysis region in the subsequent image, by calculating an evaluation value representing a degree of coincidence between the first characteristic pattern and a characteristic pattern in the subsequent image as the first characteristic pattern is moved relative to the subsequent image.

3. The non-invasive living body measuring apparatus of claim 1, wherein when the captured image is constituted by a plurality of pixels, the data processing section extracts the characteristic pattern from the captured image by calculating an average density of a local region having each pixel as its center and binarizing each pixel using the corresponding average density.

4. The non-invasive living body measuring apparatus of claim 1, wherein the characteristic pattern of the captured image is a portion of the captured image sufficient to allow for reliable pattern matching within a subsequent captured image and may include a blood vessel pattern obtained by extracting a blood vessel portion from the captured image.

5. The non-invasive living body measuring apparatus of claim 1, wherein the analysis region is repeatedly set without requiring the presence of a morphological feature within the image capture so as to contain the same blood vessel site of the same living body for obtaining information on at least one of a blood vessel dimension and a concentration of a blood cell component as the information on the living body.

6. The non-invasive living body measuring apparatus of claim 1, wherein the characteristic pattern is defined as a portion of the image capture smaller than then entire image capture and larger than the analysis region.

7. A non-invasive living body measuring method comprising the steps of:

irradiating a portion of a living body with light;

capturing an image of the irradiated portion of the living body;

setting an analysis region in the captured image to obtain information on the living body and for extracting a characteristic pattern from the captured image; and outputting the obtained information on the living body;

wherein when a first and at least one subsequent image of a portion of a living body are captured at different times and an analysis region in the first image is set, a characteristic pattern is extracted from the first image, an analysis region in the subsequent image is set based on a relative shift amount of the characteristic pattern as determined by pattern matching of the characteristic pattern within the subsequent image.

8. The non-invasive living body measuring method of claim 7, wherein the characteristic pattern is defined as a portion of the image capture smaller than then entire image capture and larger than the analysis region.

9. A non-invasive living body measuring apparatus comprising:

a light source section for irradiating a portion of a living body;

an image capturing section for capturing an image of the irradiated portion of the living body;

a data processing section for setting an analysis region in the captured image to obtain information on the living body and for extracting a characteristic pattern from the captured image;

an output section for outputting the obtained information on the living body; and an operating section for operating at least one of the image capture, data processing and output sections, wherein when the image capturing section captures images of a portion of a living body a plurality of times and the data processing section extracts a characteristic pattern from a first image, sets an analysis region in the first image, and then sets an analysis region in a subsequent image based on a relative position of the characteristic pattern in the subsequent image as determined by pattern matching within the subsequent image;

wherein the characteristic pattern of the captured image is a portion of the captured image sufficient to allow for reliable pattern matching within a subsequent captured image and may include a blood vessel pattern obtained by extracting a blood vessel portion from the captured image.

10. The non-invasive living body measuring apparatus of claim 9, wherein the data processing section determines the relative shift amount of the analysis region in the subsequent image, by calculating an evaluation value representing a degree of coincidence between the first characteristic pattern and a characteristic pattern in the subsequent image as the first characteristic pattern is moved relative to the subsequent image.

11. The non-invasive living body measuring apparatus of claim 9, wherein when the captured image is constituted by a plurality of pixels, the data processing section extracts the characteristic pattern from the captured image by calculating an average density of a local region having each pixel as its center and binarizing each pixel using the corresponding average density.

12. The non-invasive living body measuring apparatus of claim 9, wherein the analysis region is repeatedly set without requiring the presence of a morphological feature within the image capture so as to contain the same blood vessel site of the same living body for obtaining information on at least one of a blood vessel dimension and a concentration of a blood cell component as the information on the living body.

* * * * *